United States Patent [19]

Umansky et al.

[11] Patent Number: 5,516,964
[45] Date of Patent: *May 14, 1996

[54] HYDROCARBON ISOMERIZATION USING SOLID SUPERACID CATALYSTS COMPRISING PLATINUM METAL

[75] Inventors: Benjamin S. Umansky, Wilmington, Del.; Manoj V. Bhinde, Boothwyn; Chao-Yang Hsu, Media, both of Pa.

[73] Assignee: Sun Company, Inc. (R&M), Philadelphia, Pa.

[ * ] Notice: The term of this patent shall not extend beyond the expiration date of Pat. No. 5,494,571.

[21] Appl. No.: 184,154

[22] Filed: Jan. 21, 1994

[51] Int. Cl.$^6$ ............................ C07C 5/27; C10G 35/085
[52] U.S. Cl. ..................... 585/751; 585/750; 208/134; 208/135; 208/137; 208/138
[58] Field of Search ................... 208/134, 135, 208/137, 138; 585/750, 751

[56] References Cited

U.S. PATENT DOCUMENTS

| | | | |
|---|---|---|---|
| 3,708,553 | 1/1973 | Olah | 585/376 |
| 3,766,286 | 10/1973 | Olah | 585/480 |
| 3,839,489 | 10/1974 | Mahan et al. | 585/747 |
| 3,855,346 | 12/1974 | Norell | 585/747 |
| 4,918,041 | 4/1990 | Hollstein et al. | 502/217 |
| 4,956,519 | 9/1990 | Hollstein et al. | 585/751 |
| 5,019,671 | 5/1991 | Hsu et al. | 585/751 |
| 5,036,035 | 7/1991 | Baba et al. | 502/221 |
| 5,120,898 | 6/1992 | Baba et al. | 585/750 |
| 5,157,199 | 10/1992 | Soled et al. | 585/750 |

FOREIGN PATENT DOCUMENTS

| | | |
|---|---|---|
| 1076639 | 9/1993 | China . |
| 0507518A2 | 10/1992 | European Pat. Off. . |
| 0520543 | 12/1992 | European Pat. Off. . |
| 61-263932 | 11/1986 | Japan . |
| 62-246993 | 10/1987 | Japan . |
| 62-344276/49 | 10/1987 | Japan . |

OTHER PUBLICATIONS

Hino et al., "Reactions of Butane and Isobutane Catalyzed by Zirconium Oxide Treated with Sulfate Ion." *J. Amer. Chem. Soc.* (1979), 6439–41.

Hino et al., "Reactions of Butane and Isobutane Catalyzed by Titanium Oxide Treated With Sulphate Ion,"*J.S.C. Chem. Comm.* (1979), 1148–9.

Hino et al., "Synthesis of Solid Superacid Catalyst with Acid Strength of $H_o \leq -16.04$", *J.C.S. Chem. Comm.,* (1980), pp. 851–852.

Hosoi et al., "Characterization and $C_5/C_6$ Isomerization Activity of Solid Superacid ($Pt./SO_4^{2-}/ZrO_2$)" Amer. Chem. Soc. Los Angeles Meeting, Sep. 1988, *Div.Petr.Chem.Pre-.Print,* 562–567.

*Primary Examiner*—E. Rollins Cross
*Assistant Examiner*—Walter D. Griffin
*Attorney, Agent, or Firm*—Q. Todd Dickinson; Stephen T. Falk

[57] ABSTRACT

An isomerization process is provided which process utilizes a sulfated solid catalyst comprising (1) oxide or hydroxide of Group III or Group IV element, e.g. zirconium, and (2) a first metal comprising a metal or combination of metals selected from the group consisting of platinum, palladium, nickel, platinum and rhenium, and platinum and tin. The sulfated support is calcined prior to incorporation of the first metal and subsequent to said incorporation. The catalyst may further comprise (3) a second metal selected from the group consisting of Group VIII elements, e.g. iron. One embodiment of the invention further comprises (4) a third metal selected from the group consisting of Group V, VI and VII elements, e.g. manganese. Said second and third metals are added prior to the first calcination.

20 Claims, No Drawings

HYDROCARBON ISOMERIZATION USING SOLID SUPERACID CATALYSTS COMPRISING PLATINUM METAL

BACKGROUND OF THE INVENTION

This invention relates to novel processes for isomerizing a paraffin feedstock. The processes employ novel solid superacid catalysts, prepared according to a novel process utilizing at least two calcination steps. These catalysts have been found to effective in a wide variety of catalytic processes in the presence of hydrogen, including catalytic hydrocracking and naphtha upgrading processes.

BACKGROUND OF THE ART

Current commercial operations for n-butane isomerization include aluminum chloride and noble metal catalyzed processes. The aluminum chloride process, operated at relatively low temperature, is subject to corrosion and spent catalyst disposal problems. In addition, aluminum chloride processes require chloride injections to maintain acidity compensating for chloride lost to the environment. Furthermore, thermodynamic equilibrium limits the yield of isobutane. The process of the present invention causes less corrosion and has lesser environmental implications.

To obtain higher yields of isobutane, other isomerization processes have been developed. Liquid superacids containing a strong protic acid and a strong Lewis acid have been disclosed. See, U.S. Pat. Nos. 3,708,553; 3,766,286; 3,839,489; and 3,855,346.

Solid, very strongly acidic materials suitable for catalyzing hydrocarbon reactions have been prepared by others. For example, (1) Hino et al. disclose a butane isomerization catalyst prepared by treatment of zirconium oxides with sulfate ion, for example 1N sulfuric acid, and calcination of the product at 500° C. for three hours. Hino et al., "Reactions of Butane and Isobutane Catalyzed by Zirconium Oxide Treated With Sulfate Ion", J. Amer. Chem. Soc. (1979), 6439–41. Solid superacids suitable for catalyzing skeletal isomerizations of butane and isobutane have been prepared by exposing $H_4TiO_4$ to 1N sulfuric acid and calcining in air at 500° C., as disclosed in (2) Hino et al., "Reactions of Butane and Isobutane Catalyzed by Titanium Oxide Treated With Sulphate Ion", J. S. C. Chem. Comm. (1979), 1148–9. (3) Hino et al., "Synthesis of Solid Superacid Catalyst with Acid Strength of $H_o<-16.04$", J. S. C. Chem. Comm. (1980), 851–2, disclose a preparation similar to that in reference (1) above, wherein $Zr(OH)_4$ obtained from different sources was calcined at temperatures up to 650° C. and found suitable for reactions of butane in a recirculation reactor at 25° C.

In (4) Japanese patent publication 87-344276/49, a solid superacid catalyst was prepared by impregnating a carrier comprising the hydroxide or oxide or a Group III or IV metal with a Group VIII metal[1] for use in producing lower paraffin hydrocarbons from shale oil.

[1] While the abstract refers to Group VII, the examples given are only of Group VIII metals.

In (5) Hosoi et al., Amer. Chem. Soc. Los Angeles Meeting, September 1988, *Div. Petr. Chem. Pre. Print*, 561–567, $C_5$ and $C_6$ hydrocarbons are isomerized at reaction temperatures of 140° to 200° C. using sulfated zirconia superacid catalyst with and without the addition of platinum, palladium, rhodium, nickel, ruthenium, iron, tungsten or molybdenum. Isomerization activity was found to be enhanced by addition of platinum.

In (6) Baba et al., Japanese Patent No. 61-2633932, Nov. 21, 1986, filed May 17, 1985, and (7) Baba et al., U.S. Pat. No. 5,036,035, hydrocarbons are isomerized at reaction temperatures below 400° C. using a catalyst obtained by impregnating Group VIII metals, e.g. nickel, platinum, ruthenium, rhodium, palladium, osmium or iridium, and sulfate ion or precursor thereof in a carrier made of Group IV metals, e.g. titanium, zirconium, hafnium, silicon, germanium or tin, and/or hydroxide or oxide of Group III metals, e.g. aluminum, gallium, indium and thallium, and stabilizing by roasting at 450–800° C. for 5 to 16 hours. The catalysts disclosed maintained their activity over a period of 16 hours.

In (8) Ueda et al., Japanese Patent No. 62-246993, filed Apr. 2, 1986, paraffin hydrocarbons are thermally cracked at 150°–350° C. and over 50 atmospheres hydrogen pressure in the presence of a solid, highly acidic catalyst made by impregnating a Group VIII metal, e.g. nickel, platinum, ruthenium, rhodium, palladium, osmium or iridium, on a supporting body of a hydroxide or oxide of Group III or Group IV metals, e.g. titanium, zirconium, silicon, germanium, gallium or indium, followed by treating with sulfuric acid and roasting to stabilize the catalyst.

References (6), (7) and (8) indicate that addition of certain Group VIII metals improves the catalytic activities of the solid superacids and that these solid superacids are suitable for isomerization of alkanes and xylenes, and cracking of shale oil to light paraffins.

In (9) Hollstein et al., U.S. Pat. No. 4,918,041, disclose a sulfated, very strongly acidic catalyst which contains, in addition to oxide or hydroxide of Group III or Group IV element and Group VIII metal, as in references (6), (7) and (8) above, oxide or hydroxide of a Group V or Group VI or Group VII metal. This catalyst is, for example, useful in the isomerization of paraffin hydrocarbons.

In reference (9), as well as (10) Hollstein et al., U.S. Pat. No. 4,956,519, and (11) Hsu et al., U.S. Pat. No. 5,019,671, it was also shown that sulfated metal oxide catalysts are active in isomerization reactions at low temperatures without the addition of chloride compounds which create corrosion problems and environmental problems.

Low temperature isomerization processes thermodynamically favor the creation of branched paraffins. This advantage of low temperature isomerization catalysts can be diminished or lost through increased deactivation of the catalyst, even at mild reaction conditions. Under such conditions, the solid superacid catalyst can be deactivated by trace amounts of impurities in the feed or by coke precursors formed in the reaction process thereby shortening the life of the catalyst. An advantage of the catalysts of the present invention, believed to result from use of two calcination steps, is that they have extremely long life.

Two possible approaches to minimize the deactivation of the catalyst include: (1) Operating the reaction under supercritical conditions (without hydrogen and hydrogenation-type metals) so that coke precursors are dissolved in the supercritical paraffin fluids; and (2) Using hydrogenation-type metals and hydrogen that can hydrogenate coke precursors and reduce the rate of deactivation. The present invention relates to the latter approach.

SUMMARY OF THE INVENTION

The present invention provides a process for the isomerization of paraffin feedstocks, which process utilizes a sulfated, very strongly acidic catalyst comprising: (1) a support comprising Group III or Group IV oxide or hydroxide and (2) a first metal comprising a metal or mixture of metals selected from the group consisting of platinum; palladium; nickel; platinum and rhenium; and platinum and tin, and combinations thereof; wherein said sulfated support is calcined in a first calcination step before the introduction of said first metal, followed by a second calcination step.

The catalyst may further comprise Group VIII metals and/or Group V, VI or VII metals, or combinations thereof, incorporated on the support before the first calcination step. The use of at least two separate calcination steps has been found to produce superior catalysts for use in the processes of the present invention. In the presence of hydrogen, this catalyst is characterized by having high isomerization activity, as well as naphtha upgrading activity and hydrocracking activity and extremely long catalyst life.

DETAILED DESCRIPTION OF THE INVENTION

The present invention provides a novel process for the isomerization of paraffin feeds, which process utilizes catalysts comprising a sulfated solid mixture of oxide or hydroxide of Group III or IV element and a first metal comprising a metal or mixture of metals selected from the group consisting of platinum; palladium; nickel; platinum and rhenium; and platinum and tin, and combinations thereof. The composition is calcined at least once prior to introduction of said first metal and again subsequent to said introduction. The use of separate calcination steps before and after incorporation of the first metal has been found to produce unexpectedly superior catalysts with regard to both extended catalyst life and conversion activity.

The catalyst may further comprise a second metal selected from the Group VIII metals and/or a third metal selected from the Group V, VI, and VII metals. A superior catalyst is thus obtained for use, for example, in the isomerization of paraffin feeds. These catalysts have extremely long life, particularly in comparison to prior art catalysts. The support plus metal(s) can be calcined a single time prior to introduction of said first metal. Alternatively, the support can be calcined after the incorporation of each of said second and said third metals. Each of such calcination steps is performed under the conditions for the first calcination.

The catalysts of the present invention are prepared by the process of the present invention whereby the sulfated Group III or IV oxide or hydroxide, with or without the addition of said second and/or third metals, is calcined prior to the incorporation of said platinum, palladium, nickel, platinum/rhenium or platinum/tin. After incorporation of said first metal, the mixture is subjected to a second calcination. While it is contemplated that under some circumstances said second metal and said first metal may comprise the same element, they are distinct components of the catalyst by virtue of their incorporation either before or after the first calcination.

An essential element of the present invention is that the catalysts according to the invention are calcined at least twice. The first calcination is performed on the sulfated Group III or IV support with or without the addition of said second and third metals. That first calcination is carried out at a temperature in the range from 450°–800° C. for a period of 1 to 30 hours, preferably 550°–750° C., more preferably around 725° C. for a period of time in the range from 1 to 2 hours. After the incorporation of said first metal, the second calcination is carried out at a temperature in the range of 400°–700° C. for a period of 1 to 30 hours, preferably 450°–550° C. for a period of 10 hours. Preferably, the second calcination is carried out at a lower temperature than the first calcination. Combinations of temperature and time can be chosen in order to provide a desired degree of catalytic activity. For example, the catalyst prepared with a first calcination at 725° C. for 1 hour provides about the same initial conversion of n-butane to isobutane as one with a first calcination at 600° C. for 24 hours.

An advantage of the preparation process of the present invention is that it has been found to produce a more stable, long-lived catalyst. Catalyst life is particularly enhanced when the first calcination step is carried out at a higher temperature and for a shorter period of time than the second calcination step. Conducting the second calcination at temperatures above those specified above is believed to effect the stability of the catalyst by decreasing dispersion of said first metal on the support. Catalysts prepared according to the process of the present invention have been found to maintain activity for over 3000 hours. The process of the present invention is believed to maximize two of the functions of the catalyst; acidity and hydrogenation capacity.

The weight ratio of first metal to second metal is in the range 0.001:1 to 0.1:1, preferably 0.005:1 to 0.05:1. The weight ratio of third metal to second metal is in the range 0.1:1 to 2.0:1, preferably 0.2:1 to 1.0:1. The catalyst preferably contains a major amount of oxide or hydroxide of Group III or IV metal and a minor amount, preferably in the range of 0.02 to 15 weight percent, more preferably 1 to 8 weight percent, of total first metal, second metal and third metal.

The carrier or support for the catalyst according to the invention is an oxide or hydroxide of a Group III or IV element. Examples of suitable elements are titanium, zirconium, hafnium, aluminum, germanium, tin and lead. Preferred are zirconium, titanium, aluminum and silicon-aluminum and mixtures of two or more thereof. An essential component of the catalysts of the present invention is the first metal. Metals which can be used as said first metal according to the invention comprise platinum, palladium, and nickel and platinum/rhenium and platinum/tin mixtures and combinations thereof. A preferred embodiment of the catalyst comprises platinum.

The catalysts of the present invention are bifunctional catalysts; that is, they comprise metallic and acid sites which are believed to participate together in the mechanism pathways of the reforming reaction. The platinum, or other functionally equivalent metal, is believed mainly to serve as the catalytic site for hydrogenation and dehydrogenation reactions. The sulfated support is believed to provide the acid site for isomerization. Both sites are believed to participate in the hydrocracking and cyclization reactions.

One embodiment of the present invention comprises said second metal from Group VIII. Metals suitable as said second metal of the catalyst of the invention include iron, cobalt, nickel, ruthenium, rhodium, palladium, osmium, iridium and platinum and mixtures of two or more thereof. Of these, the most preferred is iron.

A further embodiment of the compositions of the present invention comprises addition of said third metal selected from Group V, Group VI and Group VII metals. Metals from Groups V, VI and VII which can be used as said third metal according to the invention comprise arsenic, antimony, bismuth, vanadium, niobium, tantalum, selenium, tellurium, chromium, molybdenum, tungsten, manganese and rhenium and mixtures of two or more thereof. Preferred among these is manganese.

The catalysts according to the invention may be prepared, for example, by sulfating a support of a Group III or IV metal oxide or hydroxide, calcining the mixture, impregnating said calcined mixture with an aqueous solution containing compounds of said first metal, and then subjecting said mixture to a second calcination. Embodiments of the catalyst of the present invention comprising additional classes of metals may be prepared by impregnating a sulfated support of a Group III or IV metal oxide or hydroxide with an aqueous solution containing compounds of said second metal, said third metal, or both said second and third metals, before the first calcination.

Alternatively, the support can be impregnated separately with solutions of the respective metal compounds. In this situation, the support plus metals can be calcined once or in separate calcination steps after the addition of each of said second metals and said third metals. In the latter process, the separate calcinations are performed under the conditions described for the first calcination step.

The catalysts according to the invention may also be prepared by co-precipitation of solid hydroxide of Group III or IV metals and the first metal and the respective second and/or third metals to be present in the catalyst, from aqueous solutions containing compounds of such metals. Again, the second and third metals present must be added before the first calcination step. The amount of the second and third metal hydroxide is typically in the range from 0.01 to 10.0 percent by weight of the total precipitated hydroxide. Mixtures of two or more Group V, Group VI and Group VII oxides or hydroxides may be employed.

The first metal is added thereafter and the mixture is then calcined again. In such method, the amount of the first metal is typically in the range from 0.01 to 50 percent by weight of the total precipitated hydroxide and varies for each metal. For platinum as first metal, the preferred range is 0.2 to 10 weight percent; for palladium, less than 1 weight percent; and for nickel, in the range of 1 to 10 weight percent.

Solutions of metal compounds which can be used in the preparation of catalysts according to the invention, by impregnation or co-precipitation, are known in the art. For example for the second and third metals, nitrates of iron and of manganese can be used, for example, to incorporate those metals in the catalyst. Solutions of zirconium oxychloride or of zirconyl nitrate can be used, for example, to prepare a zirconium support for the catalyst according to the invention. Various other solutions can be employed as needed.

Solution of said first metals which can be used in the preparation of catalysts of the present invention are also known in the art. For example, chloroplatinic acid, tetraamine-platinum complex, platinum chlorides and platinum acetylacetonate can be used to incorporate platinum in the catalyst. Nickel nitrate, nickel acetate, nickel acetylacetonate and nickel chlorides can be used to incorporate nickel in the catalyst. Palladium acetate, palladium acetylacetonate and palladium chlorides can be used to incorporate palladium in the catalyst. Rhenium nitrate, rhenium oxychloride and rhenium chlorides can be used to incorporate rhenium in the catalyst. Various other solution of platinum or the other first metals can used as needed. This impregnation can be conducted in either aqueous or organic phase.

Sulfate ion may be supplied to the catalyst according to the invention by treatment of the solid catalyst with sulfuric acid, for example, 0.01–10N sulfuric acid, preferably 0.1–5N sulfuric acid. Other compounds, such as ammonium sulfate, capable of providing sulfate ion can be employed. Compounds such as hydrogen sulfide or sulfur dioxide or mercaptans, capable of forming sulfate ions upon calcining, can also be used. Preferred catalysts for use according to the invention are those which have been sulfated with ammonium sulfate.

The catalysts according to the invention contain substantial amounts of sulfate ion, preferably amounts in the range of 0.5 to 20 weight percent based on total catalyst, preferably 2 to 8 weight percent.

Preferred catalysts according to the present invention include the following compositions: platinum/iron/$SO_4^=$/$ZrO_2$; platinum/rhenium/iron/$SO_4^=$/$ZrO_2$; platinum/rhenium/iron/manganese/$SO_4^=$/$ZrO_2$; platinum/rhenium/$SO_4^=$/$ZrO_2$; nickel/iron/$SO_4^=$/$ZrO_2$; nickel/iron/manganese/$SO_4^=$/$ZrO_2$; nickel/manganese/$SO_4^=$/$ZrO_2$; platinum/tin/iron/$SO_4^=$/$ZrO_2$; platinum/tin/iron/manganese/$SO_4^=$/$ZrO_2$.

The catalysts according to the invention may be used in a variety of hydrocarbon conversion processes, including isomerization of normal alkanes. In these processes, feed is contacted with catalyst in the presence of hydrogen. The catalysts of the present invention have been found to have an extremely long catalyst life, maintaining activity over a period of more than 3000 hours.

In one embodiment of the invention, the catalysts are used to isomerize alkanes having four to twenty, and preferably four to ten, carbon atoms, namely, butane, pentane, hexane, heptane, octane, nonane and decane, to convert the straight chain hydrocarbons into branched chain hydrocarbons having higher octane number for use as motor fuel or, as in the case of butane, having enhanced value as an intermediate for such products as tertiary butyl alcohol and high octane alkylates. In another application, the catalysts are used in the isomerization of $C_{20}$ to $C_{40}$ waxy compounds to produce lubricating oil compounds.

We have found that adding of platinum, palladium, nickel, platinum/rhenium or platinum/tin to the compositions disclosed in Hollstein et al., U.S. Pat. No. 4,918,041, and Baba et al., U.S. Pat. No. 5,036,035, and subjecting the mixture to a second calcination step produces a surprisingly superior catalyst for the isomerization of alkanes. These catalysts have an unexpectedly longer catalyst life than those of the prior art.

These solid superacid catalysts containing platinum, palladium, nickel, platinum/rhenium or platinum/tin can selectively isomerize $C_4$ to $C_{10}$ alkanes to yield highly branched alkanes without producing much $C_1$ to $C_3$ light ends. The prior art gives no indication of the superior results which may be obtained by a separate calcination step after the addition of these metals to the solid superacid catalysts comprising Group VIII metal or Group VIII metal plus Group V, VI or VII metal on a sulfated Group III or IV element support. Advantages of the catalysts according to the present invention include that they have longer life, cause less corrosion to the reaction system, produce less environmental problems than prior art catalysts and are regenerable.

The isomerization is carried out by contacting the hydrocarbon feed with the solid catalyst at temperatures in the range of 0° to 400° C., preferably in the range of 20° to 250° C., and at a pressure in the range of 15 to 1100 psig, preferably in the range of 400 to 600 psig. The isomerization is conducted in the presence of hydrogen. The mole ratio of hydrogen to hydrocarbon is preferably in the range of 0.1:1 to 10:1. Inert gas, such as nitrogen, helium or argon may be employed together with $H_2$. Generally, a temperature is used which is sufficiently high to obtain a desired rate of reaction, but not so high as to result in undesired cracking of the feed.

A preferred isomerization process comprises a pre-reduction phase and a start-up phase. The pre-reduction phase involves subjecting dry catalyst loaded into the reactor vessel to heat for a certain period of time. According to one embodiment of the process of the invention, the catalyst is dried overnight in air at a temperature in the range from 350° C. to 500° C. Subsequently, the temperature is adjusted to the pre-reduction temperature and the air is replaced with nitrogen. The pre-reduction phase is carried out in a hydrogen atmosphere. This phase is preferably conducted at pressures between atmospheric pressure and the ultimate reaction pressure.

For platinum-containing embodiments of the catalyst, the pre-reduction phase involves heating the catalyst under hydrogen to a temperature in the range from 50° to 300° C., preferably 100° to 200° C., more preferably 125° to 175° C. For nickel-containing catalysts, the pre-reduction temperature may be as high as 400° to 500° C. The duration of the pre-reduction phase is dependent on the $H_2$ flow and the amount of platinum or other first metal to be reduced. This, in turn, is a function of the size of the reactor. For example, at a flow rate of 100 cc $H_2$ per minute for a 5 cc sample of catalyst comprising 0.34% platinum, 20 minutes would be a suitable duration for the pre-reduction phase.

According to one embodiment of the process of the invention, following the pre-reduction treatment, the following reactor start-up phase conditions should be employed. The temperature of the reactor vessel is reduced to a range between room temperature and the pre-reduction temperature, the pressure is increased and the hydrocarbon feed is introduced at LHSV of 1 to 5 $hr^{-1}$. The temperature is then gradually increased at a rate of approximately 1° to 3° C. per minute until the desired isomerization reaction temperature is reached.

EXAMPLE 1

A sulfated zirconia based catalyst containing iron (Group VIII) and manganese (Group VII) was prepared by co-precipitation according to Hollstein et al., U.S. Pat. No. 4,918,041, which is incorporated herein by reference.

Zirconyl nitrate (462.46 g), ferric nitrate (26.74 g) and manganese nitrate (5.62 g) were dissolved in de-ionized water to make 1 liter of Solution A. 260 g of concentrated ammonium hydroxide were diluted with sufficient de-ionized water to make 1 liter of Solution B. 500 ml of de-ionized water were added to a 5 liter Morton flask. Solution A and Solution B were added concurrently through two addition funnels to the Morton flask slowly with rapid stirring. The temperature for the precipitation reaction was maintained at approximately 65° C. The pH of the resulting reaction mixture was maintained at approximately 7.0. The reaction slurry was filtered and the filter cake was washed with de-ionized water several times until the filtrate was nitrate free. The damp cake was applied to perforated plates, placed in a tray and dried overnight at 150° C.

The dried pellets were added slowly to a beaker containing 1.0N sulfuric acid solution at room temperature. The amount of sulfuric acid was determined by the following ratio of 15 ml of 1.0N sulfuric acid per gram of pellet. The sulfuric acid solution was decanted after the pellets had been soaked for 2 hours. The pellets were then calcined at 725° C. for 1 hour. The iron and manganese concentration in the final catalyst were 1.5% and 0.5%, respectively (Preparation I).

The pellets from Preparation I (20–40 mesh) were subsequently impregnated with an aqueous solution (incipient wetness) of chloroplatinic acid. The preparation was dried overnight at 120° C. and then calcined at 450° C. for 16 hours. The final catalyst had 0.5 weight percent platinum.

EXAMPLE 2

Sulfated zirconia based catalyst containing iron and manganese was prepared by the co-precipitation method similar to that of Example 1, except that ammonium sulfate, rather than sulfuric acid, was used to sulfate the catalyst. The sulfation was carried out prior to calcining of the catalyst. The dried pellets from the overnight drying step were treated with ammonium sulfate to incorporate 4–8% of sulfate ion in the catalyst, using incipient wetness technique, and then calcined at 725° C. for 1 hour (Preparation II).

25 g of pellets from Preparation II (20–40 mesh) were impregnated with a water solution containing nickel nitrate. This preparation was dried overnight and calcined for 16 hours between 450°–550° C. The amount of nickel in the final catalyst was 5%.

EXAMPLE 3

25 g of pellets from Preparation II (20–40 mesh) were impregnated with a water solution containing palladium chloride. This preparation was dried overnight and calcined between 450°–550° C. for 16 hours. The amount of palladium in the final catalyst was 0.5%.

EXAMPLE 4

A Pt/Fe/Mn/$SO_4^=$/$ZrO_2$ catalyst containing 0.25 wt % platinum was prepared according to the procedure of Example 1 above for use in the isomerization of a mixture of n-hexane (87%) and n-pentane (13%). Before starting the reaction, the catalyst was dried overnight at 450° C. in flowing air. Subsequently, the reactor was cooled to 150° C. and nitrogen was passed over the catalyst. This was followed by 2 hours of hydrogen flow over the catalyst and reduction of the temperature to room temperature. The reaction conditions and product distribution are presented in Table I.

EXAMPLE 5

A Pt/Fe/Mn/$SO_4^=$/$ZrO_2$ catalyst containing 0.34 wt % platinum was prepared according to the procedure of Example 1 and pre-treated as described in Example 6 above for use in the hydrocracking and isomerization of cyclohexane. The reaction conditions and product distribution are presented in Table II.

TABLE I

Isomerization of n-Hexane (87%) and n-Pentane (13%)
Catalyzed by Pt/Fe/Mn/$SO_4^=$/$ZrO_2$ with 0.25 wt % Pt

| Temp C. | 200 | 200 |
| --- | --- | --- |
| Press. PSIG | 500 | 500 |
| LHSV, 1/hr | 2 | 4 |
| H2, cc/min | 100 | 100 |
| ave. of (hrs) | 50–90 | 95–111 |
| wt % | | |
| C1 | 0.24 | 0.08 |
| C2 | 0.68 | 0.17 |
| C3 | 2.74 | 0.84 |
| I-C4 | 5.96 | 3.19 |
| N-C4 | 1.8 | 0.59 |
| I-C5 | 3.37 | 1.89 |
| N-C5 | 1.09 | 0.54 |

TABLE I-continued

Isomerization of n-Hexane (87%) and n-Pentane (13%)
Catalyzed by Pt/Fe/Mn/SO$_4^=$/ZrO$_2$ with 0.25 wt % Pt

| | | |
|---|---|---|
| 2,2DMC4 | 21.23 | 16.29 |
| 2,3DMC4 | 7.97 | 8.44 |
| 2MC5 | 26.19 | 28.54 |
| 3MC5 | 15.99 | 17.92 |
| N-C6 | 11.54 | 13.84 |
| 2,2DMC5 | 0 | 0.03 |
| 2,4DMC5 | 0.55 | 2.38 |
| 2,2,3TMC4 | 0 | 0.01 |
| 3,3DMC5 | 0 | 0.02 |
| 2MC6 | 0.06 | 0.12 |
| 2,3DMC5 | 0 | 0.04 |
| 3MC6 | 0.05 | 0.17 |
| 2,2,4-TMC5 | 0.01 | 0.1 |
| N-C7 | 0 | 0.06 |

TABLE II

Hydrocracking and Isomerization of Cyclohexane
Catalyzed by Pt/Fe/Mn/SO$_4^=$/ZrO$_2$ with 0.34 wt % Pt

| | | | |
|---|---|---|---|
| Temp. C. | 181 | 200 | 220 |
| Pres. PSIG | 500 | 500 | 500 |
| LHSV, (1/hr) | 2 | 2 | 2 |
| H2, cc/min | 100 | 100 | 100 |
| Ave. hr of wt % | 75–118 | 120–157 | 185–213 |
| Total C1-C3 | 0.24 | 0.87 | 1.77 |
| Total C4 | 5.58 | 13.97 | 20.14 |
| Total C5 | 2.22 | 7.01 | 11.6 |
| 2,2DMC4 | 1.06 | 1.99 | 2.2 |
| 2,3DMC4 | 1.18 | 1.89 | 5 |
| 2MC5 | 4.19 | 4.33 | 7.61 |
| 3MC5 | 2.55 | 3.92 | 4.61 |
| n-C6 | 2.1 | 2.94 | 3.62 |
| MCYC5 | 47.09 | 37.92 | 26.92 |
| CYC6 | 30.86 | 19.77 | 12.05 |
| Total C6+ | 3.04 | 6.76 | 13.71 |

The invention claimed is:

1. A process for isomerizing a feedstock comprising hydrocarbons having 4 to 40 carbon atoms per molecule, which process comprises contacting said feedstock, in the presence of hydrogen, with a catalyst comprising:
   (a) a sulfated support comprising oxide or hydroxide of element selected from a group consisting of Group IIIB and Group IV elements and combinations thereof; and
   (b) a first metal comprising a metal or mixture of metals selected from the group consisting of platinum; palladium; nickel; platinum and rhenium; and platinum and tin, and combinations thereof;
wherein said catalyst is prepared by the steps comprising:
   (1) calcining said sulfated support in a first calcination step;
   (2) introducing said first metal into said sulfated support; and
   (3) calcining said sulfated support and said first metal in a second calcination step;
wherein said second calcination step is carried out at a lower temperature than said first calcination step.

2. A process for isomerizing a feedstock comprising hydrocarbons having 4 to 40 carbon atoms per molecule, which process comprises contacting said feedstock, in the presence of hydrogen, with a catalyst comprising:
   (a) a sulfated support comprising oxide or hydroxide of element selected from a group consisting of Group IIIB and Group IV elements and combinations thereof;
   (b) a second metal selected from the group consisting of Group VIII metals; and
   (c) a first metal comprising a metal or mixture of metals selected from the group consisting of platinum; palladium; nickel; platinum and rhenium; and platinum and tin, and combinations thereof;
wherein said catalyst is prepared by the steps comprising:
   (1) calcining a mixture of said sulfated support and said second metal in a first calcination step;
   (2) introducing said first metal into said mixture; and
   (3) calcining said mixture and said first metal in a second calcination step;
wherein said second calcination step is carried out at a lower temperature than said first calcination step.

3. A process for isomerizing a feedstock comprising hydrocarbons having 4 to 40 carbon atoms per molecule, which process comprises contacting said feedstock, in the presence of hydrogen, with a catalyst comprising:
   (a) a sulfated support comprising oxide or hydroxide of element selected from a group consisting of Group IIIB and Group IV elements and combinations thereof;
   (b) a second metal selected from the group consisting of Group VIII metals; and
   (c) a third metal selected from the group consisting of Group V, VI and VII elements;
   (d) a first metal comprising a metal or mixture of metals selected from the group consisting of platinum; palladium; nickel; platinum and rhenium; and platinum and tin, and combinations thereof;
wherein said catalyst is prepared by the steps comprising:
   (1) calcining a mixture of said sulfated support, said second metal and said third metal in a first calcination step;
   (2) introducing said first metal into said mixture; and
   (3) calcining said mixture and said first metal in a second calcination step;
wherein said second calcination step is carried out at a lower temperature than said first calcination step.

4. The process of claim 1, 2 or 3, wherein said first calcination step is carried out at a temperature in the range of 450° to 800° C. for 1 to 30 hours.

5. The process of claim 4 wherein said temperature of said first calcination step is in the range of 550° to 750° C.

6. The process of claim 1, 2 or 3, wherein said second calcination step is carried out at a temperature in the range of 400° to 700° for 1 to 30 hours.

7. The process of claim 6 wherein said temperature of said second calcination step is in the range of 450° to 550° C.

8. The process of claim 1, 2 or 3, wherein said isomerization process is carried out with temperature in the range of 0° to 400° C., and pressure in the range of 15 to 1000 psig.

9. The process of claim 8 wherein said temperature of said isomerization process is 20° to 250° C.

10. The process of claim 8 wherein said pressure is 400 to 600 psig.

11. The process of claim 1, 2 or 3, wherein said first metal comprises platinum.

12. The process of claim 2 or 3, wherein said second metal comprises iron, cobalt, nickel, ruthenium, rhodium, palladium, osmium, iridium or platinum or mixtures thereof.

13. The process of claim 12 wherein said second metal comprises iron.

14. The process of claim 3 wherein said third metal comprises vanadium, niobium, chromium, molybdenum, tungsten, manganese, rhenium, arsenic, antimony or bismuth or mixtures thereof.

15. The process of claim 14 wherein said third metal comprises manganese.

16. The process of claim 1, 2 or 3, wherein said catalyst is subjected to a pre-reduction process comprising:

(a) drying said catalyst in air at a temperature of 350° to 500° C.;

(b) adjusting said temperature to a pre-reduction temperature in the range of 50° to 500° C.;

(c) purging said air with $N_2$;

(d) replacing said $N_2$ with $H_2$; and (e) reducing said catalyst in $H_2$ at said pre-reduction temperature at a pressure of 15 to 1100 psig.

17. The process of claim 1, 2 or 3, wherein said feedstock comprises hydrocarbons having 4 to 10 carbon atoms per molecule.

18. The process of claim 1, 2 or 3, wherein said feedstock comprises hydrocarbons having 20 to 40 carbon atoms per molecule.

19. The process of claim 2 wherein said first calcination step comprises separately calcining said mixture subsequent to the introduction of each of said second metal or metals.

20. The process of claim 3 wherein said first calcination step comprises separately calcining said mixture subsequent to the introduction of each of said second metal or metals and each of said third metal or metals.

\* \* \* \* \*